United States Patent [19]

Chubachi

[11] Patent Number: 4,491,020
[45] Date of Patent: Jan. 1, 1985

[54] ULTRASONIC MICROSCOPE
[75] Inventor: Noriyoshi Chubachi, Miyagi, Japan
[73] Assignee: Keisuke Honda, Miyagi, Japan
[21] Appl. No.: 439,586
[22] Filed: Nov. 5, 1982
[30] Foreign Application Priority Data Nov. 13, 1981 [JP]  Japan ................... 56-182710

[51] Int. Cl.³ ............................................. G01N 29/00
[52] U.S. Cl. ......................................... 73/606; 73/618
[58] Field of Search ............... 73/597, 598, 606, 607, 73/618

[56] References Cited

U.S. PATENT DOCUMENTS 4,028,933 6/1977 Lemons et al. ................ 73/627
4,030,342 6/1977 Bond et al. ..................... 73/620
4,147,064 4/1979 Bond ............................... 73/597

Primary Examiner—Stephen A. Kreitman
Assistant Examiner—John E. Chapman, Jr.
Attorney, Agent, or Firm—Burgess, Ryan and Wayne

[57] ABSTRACT

An ultrasonic microscope is provided wherein a sample placed in a medium is irradiated with a focused ultrasonic wave from a focusing ultrasonic transmitting element and the focused ultrasonic wave is detected by a focusing ultrasonic receiving element. The sample (or the focusing transmitting element and the focusing ultrasonic receiving element) is moved within the X-Y plane, and either the focusing transmitting element or the focusing ultrasonic receiving element is vibrated toward the sample along the beam axis.

5 Claims, 5 Drawing Figures

ULTRASONIC MICROSCOPE

BACKGROUND OF THE INVENTION

The present invention relates to a transmission ultrasonic microscope which radiates ultrasonic waves into an object to be measured and which detects changes in the velocity of the ultrasonic waves propagating in the object by a focusing ultrasonic receiving element in accordance with interferometry principles.

The present inventor has previously proposed an improvement over a conventional ultrasonic microscope of confocal assembled type which uses focusing concave transducers at the radiating and detecting sides. According to the proposed ultrasonic microscope, a plane ultrasonic transducer is used at the radiating side and a focusing concave ultrasonic transducer is used at the detecting side.

However, in this proposed ultrasonic microscope, since the radiating area of the plane ultrasonic transducer is wide, the required electric power increases. Furthermore, radiation of ideal plane waves is not easy, and the sound field tends to become nonuniform due to diffraction. Adjustment of the tilt angle of the plane ultrasonic transducer is time-consuming, and interference tends to be caused between a flat sample and the plane ultrasonic transmitter.

SUMMARY OF THE INVENTION

It is an object of the present invention to provide an ultrasonic microscope which provides good detection precision and which is improved in workability.

In order to achieve the above and other objects of the present invention, there is provided an ultrasonic microscope wherein an object to be tested is radiated with a focused ultrasonic wave from a focusing ultrasonic transmitting element, an ultrasonic wave which is changed inside the object is detected at a small portion of the object by a focusing ultrasonic receiving element, the focusing ultrasonic transmitting element and the focusing ultrasonic receiving element or the object are or is moved within an X-Y plane by a X-Y scanner, and one of the focusing transmitting and receiving elements is vibrated toward the object or along the beam axis by a vibrator.

DETAILED DESCRIPTION OF THE PREFERRED EMBODIMENTS

Figure 1:
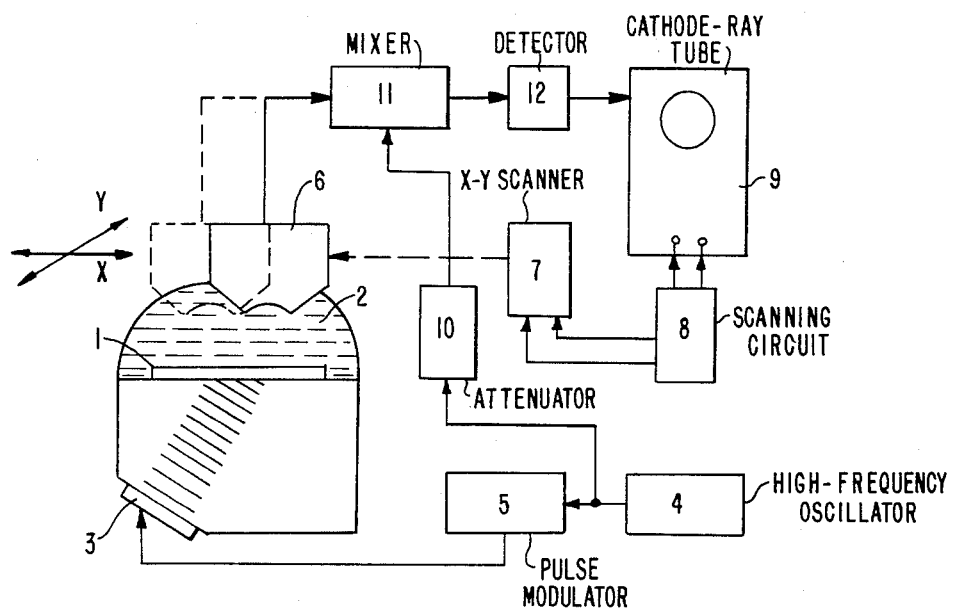
FIG. 1 is a block diagram of an ultrasonic microscope previously proposed by the present inventors.

A microscope previously proposed by the present inventor will first be described. FIG. 1 is a block diagram of this ultrasonic microscope. Referring to FIG. 1, a sample 1 is placed in a medium 2. A plane ultrasonic transmitting element 3 is arranged obliquely with respect to the vertical axis of the sample 1. A continuous electric signal from a high-frequency oscillator 4 is converted into a high-frequency pulse by a pulse modulator 5. The high-frequency pulse from the pulse modulator 5 is supplied to the plane ultrasonic transmitting element 3 to radiate the ultrasonic waves onto the sample 1. A focusing ultrasonic receiving element 6 is arranged to oppose the plane ultrasonic transmitting element 3 through the sample 1 interposed therebetween. The focusing ultrasonic receiving element 6 is coupled to an X-Y scanner 7 which is moved along the X- and Y axes in response to a signal from a scanning circuit 8. The signal from the scanning circuit 8 is also supplied to a cathode-ray tube 9 (to be referred to as a CRT for brevity hereinafter). The ultrasonic waves which have been transmitted through the sample 1 are received by the focusing ultrasonic receiving element 6 and are converted into an electric signal. The electric signal is then mixed by a mixer 11 with a reference signal which is produced from the high-frequency oscillator 4 which is attenuated by an attenuator 10 to the level of the electric signal from the focusing ultrasonic receiving element 6. The composite signal, that is the interference signal from the mixer 11 is rectified by a detector 12 and is supplied to the intensity modulation input terminal (z-axis) of the CRT 9 to be displayed thereby.

In an ultrasonic microscope of the arrangement as described above, since the radiating area of the plane ultrasonic transmitting element 3 is wide, the electric power consumption is increased, and radiation of ideal plane waves is difficult. Furthermore, the sound field tends to become nonuniform, and adjustment of the tilt angle of the plane ultrasonic transducer is time-consuming. Moreover, interference tends to occur between the flat sample 1 and the plane ultrasonic transmitting element 3.

Figure 2:
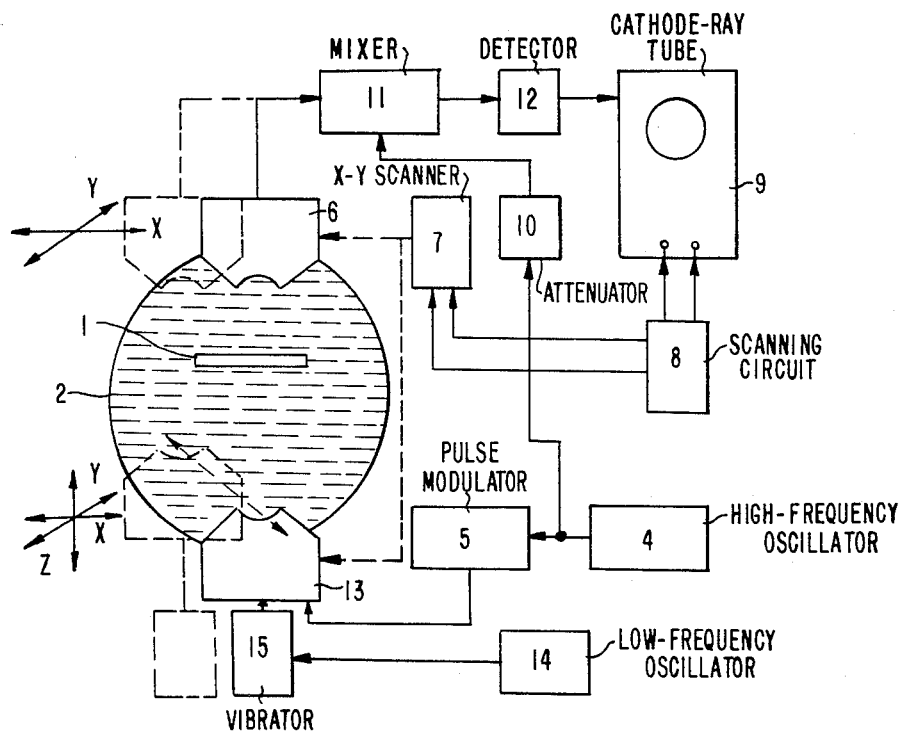
FIG. 2 is a block diagram of an ultrasonic microscope according to a first embodiment of the present invention.

FIG. 2 shows a block diagram of an ultrasonic microscope according to the first embodiment of the present invention. The same reference numerals as in FIG. 1 denote the same parts in FIG. 2. However, in the embodiment of the present invention, a focusing ultrasonic transmitting element 13 is used in place of the plane ultrasonic transmitting element 3. The focusing ultrasonic transmitting element 13 is moved together with the focusing ultrasonic receiving element 6 in the X-Y plane by the X-Y scanner 7. The focusing ultrasonic transmitting element 13 is vibrated in the direction toward the sample 1, that is, along the z-axis by a vibrator 15 which is driven by a low-frequency signal from a low-frequency oscillator 14. This is done to effectively incline the resulting transmitted ultrasonic wave with respect to the sample 1.

Figure 3:
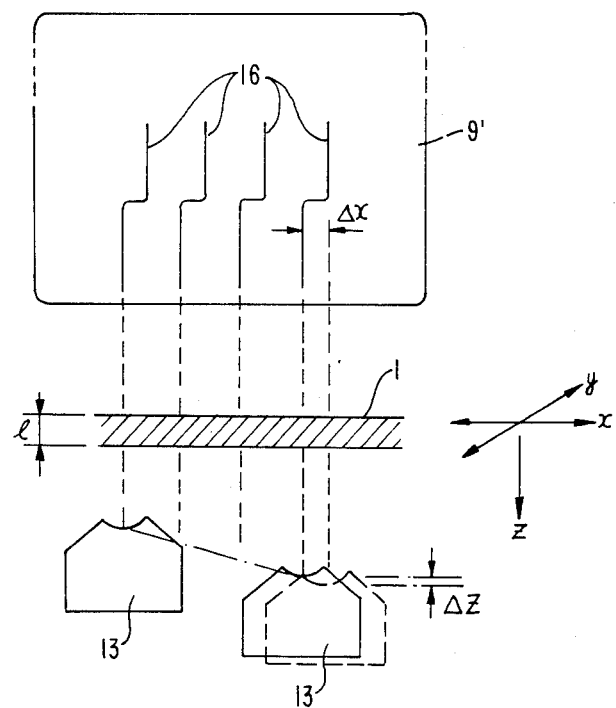
FIG. 3 is a view for explaining the mode of operation of the microscope shown in FIG. 2.

In the ultrasonic microscope of the embodiment of the arrangement as described above, the relative changes between the sample 1 and the ultrasonic beam acts as if the radiating surface of the focusing ultrasonic transmitting element 13 is inclined with respect to the sample 1 as shown by the broken line in FIG. 2, if the lateral movement along the X-axis of the ultrasonic transmitting element 13 is synchronized with the change in the distance between the focusing ultrasonic transmitting element 13 and the sample 1; that is, the rate of change in the length of the propagation path of the ultrasonic waves determined by the vibrator 15. In this manner, the interference pattern of the ultrasonic waves is displayed on the screen of the CRT in accordance with the same principle as in the prior art. That is, the interference signal is generated by the mixer 11, which combines the (attenuated) reference signal output of the oscillator 4 with the signal from the receiving element 6, the latter signal being delayed in phase from the reference signal due to ultrasonic propagation delay through the medium 2 and sample 1. More particularly, the surface of the sample 1 is scanned by the ultrasonic beam along the X-axis. The screen of the CRT is scanned along the X-axis (horizontal axis) in correspondence with the scanning operation of the sample 1. The output from the mixer 11 is supplied to the z-axis (intensity modulation axis) of the CRT 9. The ultrasonic beam is further scanned along the Y-axis to raster-scan the sample 1. Then, interference fringes 16 displayed on a screen 9′ of the CRT 9 partially fluctuate as shown in FIG. 3, due to variation in ultrasonic propagation velocity through different parts of the sample 1. The two-dimensional distribution of the velocity of sound in the sample 1 may be measured from the fluctuation.

Figure 4:
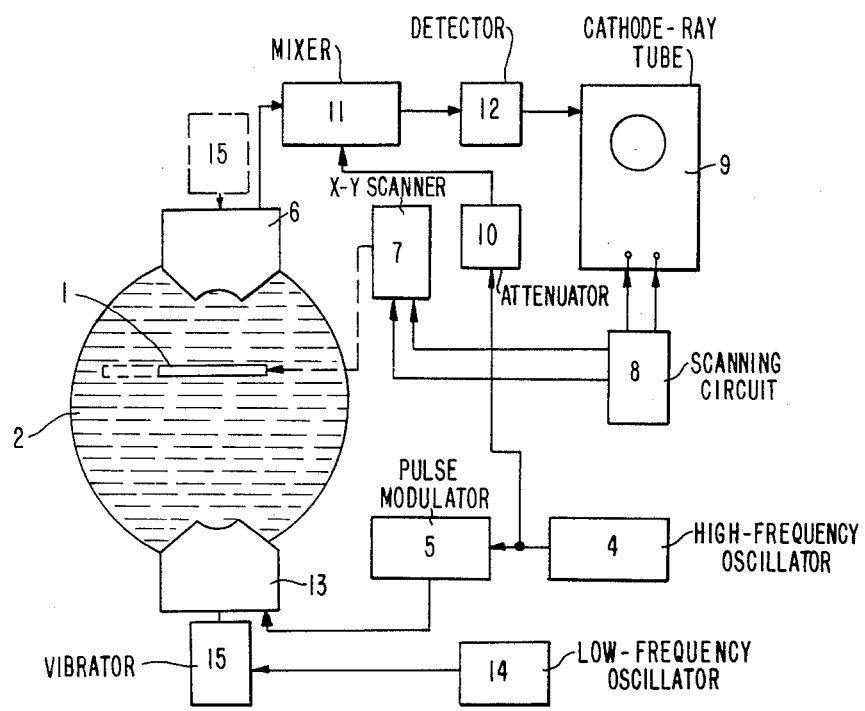
FIG. 4 is a block diagram of an ultrasonic microscope according to a second embodiment of the present invention.

FIG. 4 shows a block diagram of an ultrasonic microscope according to another embodiment of the present invention. According to this embodiment, the sample 1 is moved within the X-Y plane by the X-Y scanner 7. The ultrasonic transmitting element 13 is vibrated by the vibrator 15, or the ultrasonic receiving element 6 is vibrated by a vibrator 15 indicated by the broken line, along the Z-axis.

An experiment conducted with regard to the embodiment shown in FIG. 4 will now be described.

The frequency of the ultrasonic waves was 100 MHz. The sample was a part of myocardial tissue which had a thickness of 20 μm. A pair of concave ultrasonic transducers comprising a pair of zinc oxide (ZnO) piezoelectric films was used as the focusing ultrasonic transmitting element 13 and the focusing ultrasonic receiving element 6. Both elements had a focal length of 1,500 μm to have a common focal point. The sample 1 was mechanically sinusoidally vibrated at a frequency of 50 Hz by an electric coil with a scanning amplitude B of 1 mm as the X-axis scanning. In synchronism with the X-axis scanning, the focusing ultrasonic receiving element was vibrated by the vibrator at a frequency of 50 Hz along the Z-axis with an amplitude A of ±100 μm with the point of equilibrium as the center. The length of the propagation path between the focusing transmitting and receiving elements was varied. Further, the mount of the electric coil for X-axis scanning was moved along the Y-axis for 2 mm within a time period of about 10 sec to two-dimensionally scan the sample with the ultrasonic beam. The interference fringes displayed on the screen of the CRT were shifted at the boundary between the sample and water as the reference medium (velocity of sound v=1,510 m/sec). The shift of the interference fringes on the screen of the CRT was measured to be $\Delta x = 32$ μm when it was calculated in terms of the distance on the surface of the sample. Let l represent the thickness of the sample, $v_0$ and $v_1$ represent the velocities of sound in the reference medium and the sample, and $\Delta Z$ represent the amount of change in the length of the propagation path, then $$\Delta Z = l(1 - v_0/v_1)$$

Therefore, $$v_1 = v_0/(1 - \Delta Z/l)$$

Since $$\Delta Z = \Delta x \times (A/B) = 3.2 \ \mu m$$

$$l = 20 \ \mu m$$

the velocity of sound in the sample at the boundary with water is given by:

$$v_1 = 1510/(1 - 3.2 \times 10^{-6}/20 \times 10^{-6}) = 1800 \ (m/sec)$$

In this manner, the distribution of velocity of sound at the inner part of the sample apart from the boundary between the sample and water may be easily measured from the shift of the interference fringes.

Figure 5:
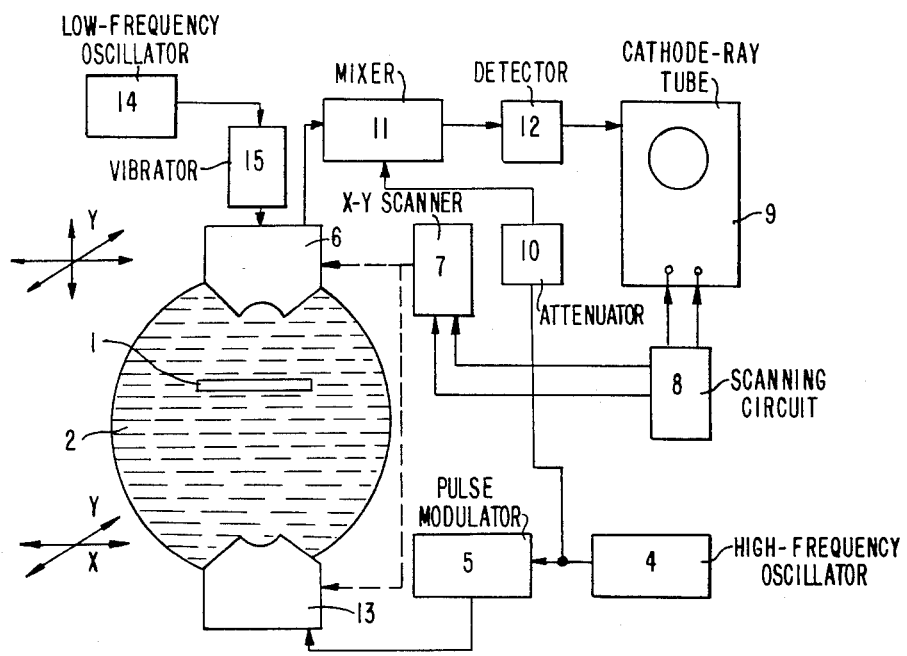
FIG. 5 is a block diagram of an ultrasonic microscope according to a third embodiment of the present invention.

FIG. 5 shows a block diagram of an ultrasonic microscope according to still another embodiment of the present invention. In this embodiment, the focusing ultrasonic receiving element 6 and the focusing ultrasonic transmitting element 13 is moved within the X-Y plane by the X-Y scanner 7, and the focusing ultrasonic transmitting element 6 is moved by the vibrator 15 along the Z-axis. The mode of operation and effects of this embodiment are the same as those of the former embodiments, and a description thereof will be omitted.

In the embodiments described above, the continuous electric signal from the high-frequency oscillator 4 is modulated into a high-frequency pulse by the pulse modulator 5. However, the ultrasonic wave to be radiated in the medium (water) 2 need not be a pulsed ultrasonic wave and may be a continuous ultrasonic wave.

In summary, according to the present invention, since the radiation of the ultrasonic waves is performed by the focusing ultrasonic transmitting element, efficiency of the microscope is good, and the input power is decreased. Furthermore, the effective tilt angle may be freely and easily changed by electrically changing the ratio of the vibration amplitude of the focusing transmitting or receiving element along the Z-axis to the vibration amplitude of the sample along the X-axis. Since focused ultrasonic waves are utilized, standing wave interference does not occur, providing an effective ultrasonic microscope.

What is claimed is:

1. An ultrasonic microscope for scanning a sample disposed in a medium, comprising:
    a focusing ultrasonic transmitting transducer element adapted to be coupled to said medium for generating a focused ultrasonic wave to irradiate a small portion of said sample, in response to a drive signal of ultrasonic frequency;
    a focusing ultrasonic receiving transducer element adapted to be coupled to said medium for generating a received signal in response to ultrasonic waves generated by said transmitting element and propagated through said small portion of said sample;
    reference signal generating means for providing a reference signal of ultrasonic frequency;
    drive means responsive to said reference signal for generating said drive signal of ultrasonic frequency to drive said transmitting element;
    X-Y axis scanning means for causing said focused ultrasonic wave to scan or traverse said sample in a coordinate plane substantially perpendicular to a line extending between said transmitting and receiving elements, while maintaining said elements in mutual alignment along said line;

mixer means for combining said received signal with said reference signal to produce an interference signal; and Z axis scanning means for vibrating one of said transmitting and receiving elements along the direction of said line extending between said transmitting and receiving elements, in synchronism with the scanning of said sample by said X-Y axis scanning means, whereby said ultrasonic beam is caused to impinge upon said sample as if the radiating surface of said transmitting element is inclined with respect to said line extending between said transmitting and receiving elements, the apparent inclination of said radiating surface being variable by varying the amplitude of vibration by said Z axis scanning means relative to the amplitude of scanning by said X-Y axis scanning means.

2. The ultrasonic microscope according to claim 1, wherein said X-Y axis scanning means moves the sample, said transmitting and receiving elements having no scanning movement in the X and Y directions.

3. The ultrasonic microscope according to claim 1, wherein said drive signal is a continuous wave signal.

4. The ultrasonic microscope according to claim 1, wherein said drive signal is a pulse signal.

5. The ultrasonic microscope according to claim 1, further comprising means for simultaneously displaying the X axis position of said ultrasonic beam relative to said sample, the Y axis position of said ultrasonic beam relative to said sample, and said interference signal.

* * * * *